United States Patent [19]

Pellicano et al.

[11] Patent Number: 4,592,371
[45] Date of Patent: Jun. 3, 1986

[54] MUSCLE TESTING METHOD

[75] Inventors: Russell A. Pellicano, N. Bay Shore, N.Y.; Daniel DelGiorno, Fort Lee, N.J.

[73] Assignee: Prestigeline Health Products Inc., Brentwood, N.Y.

[21] Appl. No.: 621,162

[22] Filed: Sep. 24, 1984

[51] Int. Cl.⁴ .............................................. A61B 5/10
[52] U.S. Cl. ...................................... 128/774; 73/379
[58] Field of Search ............... 128/728, 774, 778, 779, 128/781; 73/172, 379–381; 272/67, 94, 96, 99

[56] References Cited

U.S. PATENT DOCUMENTS

| | | | |
|---|---|---|---|
| 482,623 | 9/1892 | Dooling | 272/76 |
| 2,708,367 | 5/1955 | Lusk | 73/379 |
| 2,839,050 | 6/1958 | Sokol | 128/778 |
| 3,482,564 | 12/1969 | Robinson | 128/774 |
| 4,231,255 | 11/1980 | Haski et al. | 73/379 |

Primary Examiner—William E. Kamm

[57] ABSTRACT

A method for testing isolated muscles for comparative strength and endurance using an air bag to measure upon the application of force by the muscle the maximum pressure reached and maintained for a preselected period of time.

3 Claims, 3 Drawing Figures

MUSCLE TESTING METHOD

BACKGROUND OF THE INVENTION

This invention comes within the field of physical testing of muscles.

Current testing of muscles at the isolated level requires a doctor or physical therapist. To gauge muscle strength the tester must rely completely on judgment while applying force against the muscle to be tested. No basis for retest is obtained in this manner. In other words, the very subjective nature of current testing procedures makes it difficult and unreliable to compare test results taken at different times or with different subjects.

SUMMARY OF THE INVENTION

The present invention makes it possible to test isolated muscles or groups of muscles for comparative strength and endurance measuring through the use of an air bag the pressure caused by the muscle and the length of time that the pressure can be maintained. The pressure reading and the length of time that the pressure can be maintained in the given range of pressure determines the relative strength and endurance of the tested muscle.

In an embodiment of the invention there is provided an objective method of testing a muscle for comparative strength and endurance comprising the steps of pressurizing a sealed container with a gas to a predetermined pressure, utilizing said muscle to press a limb against said container in a manner to compress said container thereby raising the pressure therewithin, and measuring the rise in pressure and duration of said rise within said container in order to produce an indicator of the strength of said muscle.

DETAILED DESCRIPTION OF THE PREFERRED EMBODIMENTS

Figure 1:
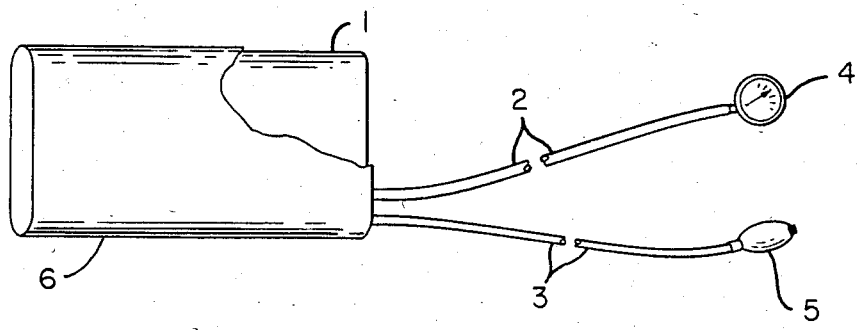
FIG. 1 shows the muscle testing device's component parts.

Referring to FIG. 1, the device shown consists of the following parts:
1. Rubber or plastic air bag, currently 7 in.×9 in. in size, but may be larger or smaller depending on testing requirements.
2. Connecting hose from air bag to pressure gauge.
3. Connecting hose from air bag to blow-up bulb (blow-up bulb may be eliminated for inexpensive models).
4. Pressure gauge (air).
5. Blow-up bulb and valve (may be eliminated for inexpensive models).
6. Protective canvas or material covering.

The air bag 1 is blown up by forcing air from the blow-up bulb 5, or mouth of user through the connecting hose 3. The gauge 4 is monitored to read two to three pounds of pressure. Testing may proceed from this starting point.

Figure 2:
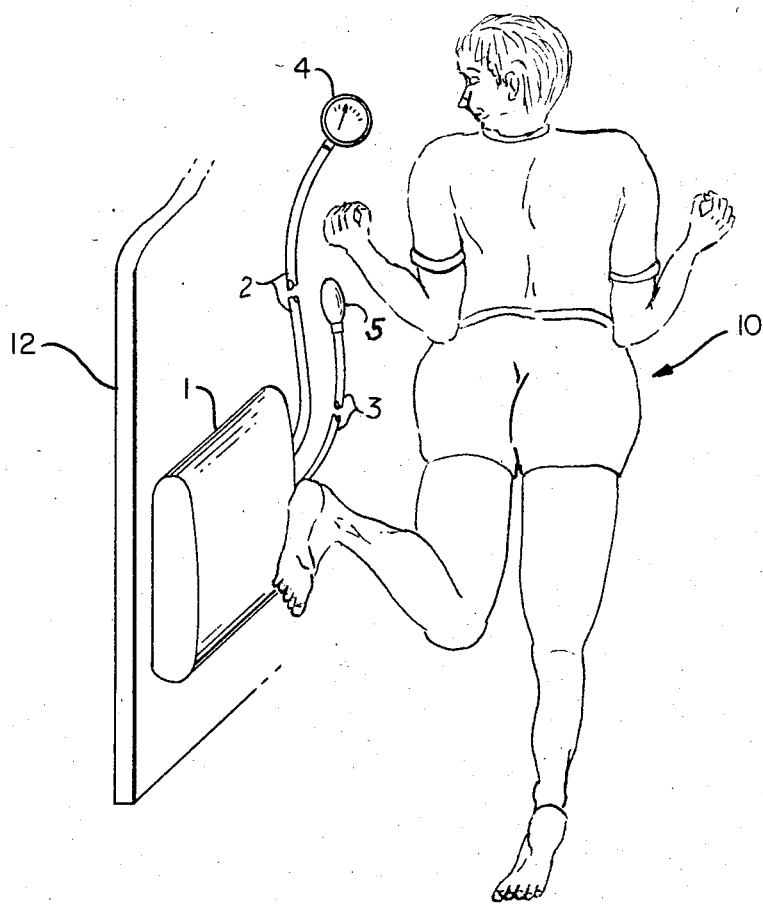
FIG. 2 is an isometric view of the muscle testing device in use.
Figure 3:
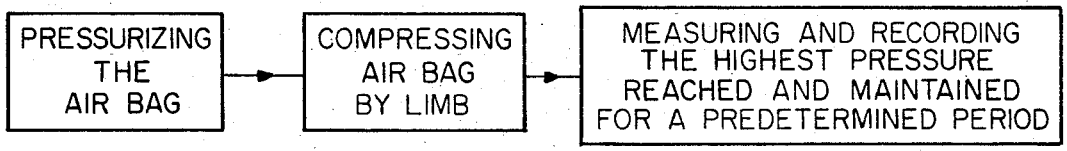
FIG. 3 is a flow chart illustrating the method steps of this invention.

FIG. 2 shows the testing of the Iliacus muscle (isolated). Air bag 1 is mounted on a support 12. Not shown in FIG. 2 is the bulb 5 which as noted above is used to inflate the bag 1 to some initial pressure.

In the operation of the device shown in FIG. 2, person 10 lies face down, bends his knee 90°, turns lower leg to the side, presses it as shown against air bag 1, and the reading is obtained from gauge 4.

Test results are recorded as follows: Record the highest number person 10 can hold fixed for three seconds; this number gives the base to start with. The number recorded is the gauge of muscle strength. If the person 10 holds the pressure at a fixed number for as long as he can, this will give a recording of muscle endurance. Then the same muscle is retested in proportion to the effort and frequency it is being worked (i.e., weekly, biweekly, or monthly). If the muscle does not increase in strength the program is adjusted.

Testing diagrams are helpful in demonstrating the resistance needed to build strength and endurance to individual muscles. If you isolate the muscle to be worked on, your efforts will be used in developing those muscles you have trouble with. The fastest route to maximum achievement is to direct your efforts on a sound course. The course must be monitored to receive maximum results in a short period of time.

In accordance with this invention, muscle testing takes only minutes, and it takes the trial and error out of a fitness program.

The following sums up the applications and benefits of this invention:

PROFESSIONALS
  Doctors
  Therapists
  Sports Trainers
  Health Spas
GENERAL PUBLIC
  Exercise
  Body Development
  Maintaining Fitness When time, money, and effort is spent on accomplishing something it makes good sense to monitor the progress. A scale is as important to a person on a diet as a muscle tester is to a person improving their muscle strength. Whether the purpose is for fitness or health, goals must be set and progress monitored.

BENEFITS
  Motivation
  Being insured your program is beneficial.
  If any injury occurs what effect has it had on your muscle strength.
  Know when your muscles are at their peak.
  Being able to isolate each muscle to test their improvement.
  Record changes

VALUE IN ISOLATING, TESTING, AND RECORDING MUSCLE AND ENDURANCE CHANGES:

DOCTORS
  Record changes in muscle strength in cases such as; disuse atropy, stroke, paralysis, nerve degeneration, injury to muscle and joints, record strength prior to surgery, and recheck periodically to determine recovery and progress, any condition where muscle strength or endurance is indicitive of patients recovery.
THERAPIST
  Isolate and record muscle strength prior to therapy, indication of progress, be more specific in therapy planning, if injured muscle or joints are not responding in reasonable time testing could save time detecting a possible complication of nerve damage.

SPORTS TRAINERS

The same as for therapists. Having a record of strength on your athletes could be a very valuable asset such as; what effect did an injury have on your athlete, are they back to their normal strength level before going back into competition, which muscles need more strength and endurance, will provide motivation for your athletes when they can see improvement, at times other illness will affect muscle strength having a record of their normal strength could be crucial in an important event.

HEALTH SPAS

When people can record progress their motivation to continue is high, when changes are seen weekly the amount of people dropping out of programs will be reduced. In most cases before physical change is noticed on a person muscle strength has improved but not enough for a person to get compliments on their appearance.

The muscle tester will pick up the slightest increase of muscle strength. The professionals could more accurately prescribe change in exercise to show increased progress. Seeing is believing when they can record the change they stay motivated. When testing individual muscles rather than gereral strength the chance to overlook muscles that one assumes are being worked on becomes much less. Working on those individual muscles could be a great asset.

GENERAL PUBLIC

For people who exercise at home recording progress of muscle strength and endurance has all the benefits listed above.

What is claimed is:

1. An objective method of testing a muscle for comparative strength and endurance in a person comprising the steps of fixedly supporting and pressurizing a sealed container with a gas to a predetermined pressure thereby rendering said container compressible, allowing said person to press a limb in one direction only against said container to compress said container thereby raising the pressure therewithin, recording the highest pressure maintained by said person for a predetermined specific period of time, and subsequently repeating the aforesaid steps to obtain comparative information.

2. The method of claim 1 in which said specific period of time is three seconds.

3. In the method of claim 1 repeating said steps at regular intervals in order to indicate the course of change in muscle strength of said person.

* * * * *